United States Patent
Popp et al.

(10) Patent No.: US 6,817,994 B2
(45) Date of Patent: Nov. 16, 2004

(54) ABSORBENT ARTICLE WITH REFASTENABLE SIDES

(75) Inventors: Robert Lee Popp, Hortonville, WI (US); Joseph D. Coenen, Neenah, WI (US); Jack L. Couillard, Menasha, WI (US); Christopher Peter Olson, Neenah, WI (US); David Arthur Kuen, Neenah, WI (US); Shawn A. Quereshi, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/205,756

(22) Filed: Jul. 26, 2002

(65) Prior Publication Data

US 2003/0018315 A1 Jan. 23, 2003

Related U.S. Application Data

(62) Division of application No. 09/572,665, filed on May 16, 2000.

(51) Int. Cl.⁷ .............................................. A61F 13/15
(52) U.S. Cl. ...................................... 604/389; 604/391
(58) Field of Search ....................... 604/385.01, 389.23, 604/389.24, 386, 391, 390, 306, 385.22, 389

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,692,618 A | 9/1972 | Dorschner et al. |
| 3,772,120 A | 11/1973 | Radzins |
| 3,802,817 A | 4/1974 | Matsuki et al. |
| 3,849,241 A | 11/1974 | Butin et al. |
| 4,081,301 A | 3/1978 | Buell |
| 4,145,763 A | 3/1979 | Abrams et al. |
| 4,205,679 A | 6/1980 | Repke et al. |
| 4,340,563 A | 7/1982 | Appel et al. |
| 4,402,690 A | 9/1983 | Redfern |
| 4,610,680 A | 9/1986 | LaFleur |
| 4,615,695 A | 10/1986 | Cooper |
| 4,617,022 A | 10/1986 | Pigneul et al. |
| 4,641,381 A | 2/1987 | Heran et al. |
| 4,646,362 A | 3/1987 | Heran et al. |
| 4,650,530 A | 3/1987 | Mahoney et al. |

(List continued on next page.)

FOREIGN PATENT DOCUMENTS

| | | |
|---|---|---|
| EP | 217 032 | 4/1987 |
| EP | 262 447 | 4/1988 |
| EP | 860 159 | 8/1998 |
| EP | 757 550 | 12/1998 |
| GB | 1 520 740 | 8/1978 |
| GB | 2 296 179 | 6/1996 |
| GB | 2 303 045 | 2/1997 |
| WO | 95/27461 | 10/1995 |
| WO | 95/27462 | 10/1995 |
| WO | 97/23180 | 7/1997 |
| WO | 97/46197 | 12/1997 |
| WO | 00/23025 | 4/2000 |
| WO | 00/35398 | 6/2000 |
| WO | 00/37009 | 6/2000 |

*Primary Examiner*—John J. Calvert
*Assistant Examiner*—C. Lynne Anderson
(74) *Attorney, Agent, or Firm*—Pauley Petersen & Erickson

(57) ABSTRACT

A pant-like absorbent garment adapted to easy application and removal has refastenable side seams. The refastenable side seams extend from a waist opening to each of two leg openings between a front panel and a back panel. Each of the refastenable side seams includes a fastening component and a mating fastening component, each of which comprises either a hook material or a loop material. A portion of the mating fastening component can be die-cut in a sinusoidal or other nesting shape. The resulting refastenable seams can be lap seams, dual fastened lap seams, standing butt seams, or dual fastened standing butt seams.

14 Claims, 14 Drawing Sheets

U.S. PATENT DOCUMENTS

| | | | |
|---|---|---|---|
| 4,663,220 A | 5/1987 | Wisneski et al. | |
| 4,694,978 A | 9/1987 | Westphal et al. | |
| 4,699,622 A | 10/1987 | Toussant et al. | |
| 4,704,116 A | 11/1987 | Enloe | |
| 4,739,910 A | 4/1988 | Westphal et al. | |
| 4,892,598 A * | 1/1990 | Stevens et al. | 156/91 |
| 4,904,251 A | 2/1990 | Igaue et al. | |
| 4,936,840 A | 6/1990 | Proxmire | |
| 4,940,464 A | 7/1990 | Van Gompel et al. | |
| 5,034,007 A | 7/1991 | Igaue et al. | |
| 5,046,272 A | 9/1991 | Vogt et al. | |
| 5,049,145 A | 9/1991 | Flug | |
| 5,087,253 A | 2/1992 | Cooper | |
| 5,104,116 A | 4/1992 | Pohjola | |
| 5,224,405 A | 7/1993 | Pohjola | |
| 5,226,992 A | 7/1993 | Morman | |
| 5,342,341 A | 8/1994 | Igaue et al. | |
| 5,370,634 A * | 12/1994 | Ando et al. | 604/385.21 |
| 5,374,262 A | 12/1994 | Keuhn, Jr. et al. | |
| 5,624,428 A * | 4/1997 | Sauer | 604/391 |
| 5,645,543 A | 7/1997 | Nomura et al. | |
| 5,693,165 A | 12/1997 | Schmitz | |
| 5,779,831 A | 7/1998 | Schmitz | |
| 5,785,699 A | 7/1998 | Schmitz | |
| 5,795,350 A | 8/1998 | Schmitz | |
| 5,830,206 A | 11/1998 | Larsson | |
| 5,855,574 A | 1/1999 | Kling et al. | |
| 5,897,545 A | 4/1999 | Kline et al. | |
| 5,899,896 A | 5/1999 | Suprise et al. | |
| 5,957,908 A | 9/1999 | Kline et al. | |
| 5,961,761 A | 10/1999 | Heindel et al. | |
| 6,022,432 A | 2/2000 | Elsberg et al. | |
| 6,210,388 B1 | 4/2001 | Widlund et al. | |
| 6,213,991 B1 * | 4/2001 | Kling et al. | 604/385.01 |
| 6,287,287 B1 | 9/2001 | Elsberg | |
| 6,328,725 B2 | 12/2001 | Fernfors | |
| 6,395,115 B1 | 5/2002 | Popp et al. | |
| 6,409,858 B1 | 6/2002 | Popp et al. | |
| 6,413,249 B1 * | 7/2002 | Turi et al. | 604/387 |
| 6,432,243 B1 | 8/2002 | Popp et al. | |
| 6,432,248 B1 | 8/2002 | Popp et al. | |
| 6,447,628 B1 | 9/2002 | Couillard et al. | |
| 6,454,752 B1 | 9/2002 | Huang et al. | |
| 6,461,344 B1 | 10/2002 | Widlund et al. | |
| 6,481,362 B2 | 11/2002 | Hietpas et al. | |
| 6,497,032 B2 | 12/2002 | Maxton et al. | |
| 6,513,221 B2 | 2/2003 | Vogt et al. | |
| 6,514,187 B2 | 2/2003 | Coenen et al. | |
| 6,520,947 B1 * | 2/2003 | Tilly et al. | 604/391 |

* cited by examiner

ABSORBENT ARTICLE WITH REFASTENABLE SIDES

This is a Divisional of pending U.S. patent application Ser. No. 09/572,665, filed May 16, 2000.

FIELD OF THE INVENTION

This invention is directed to pant-like, personal care absorbent products having hook and loop fasteners on the side panels for ease of removal and donning without complete removal of a wearer's clothing.

BACKGROUND OF THE INVENTION

Pant-like absorbent garments, such as adult incontinence wear as well as infant and children's diapers, swim wear and training pants, typically have adhesive fasteners on the sides for donning and removal, or else rely on the waist opening and leg openings to slide on and off the wearer. Adhesive fasteners wear out in as little as one use. Therefore, if a care giver checks the status of the wearer's absorbent garment contents by unfastening an adhesive fastener, the garment often must be replaced due to a worn out adhesive fastener even if the absorbent garment itself is not in need of changing.

Absorbent garments that slide on and off a wearer are often messy when full. Furthermore, in order to remove such absorbent garments, the wearer's clothing covering the absorbent garments, such as pants, must be completely removed. Checking the status of the wearer's absorbent garment contents is often just as cumbersome as changing the absorbent garment.

There is a need or desire for pant-like, personal care absorbent garments that have refastenable side seams for ease of removal and donning without complete removal of a wearer's clothing.

SUMMARY OF THE INVENTION

The present invention is directed to pant-like absorbent garments having hook and loop fasteners applied at the sides of the garments. The resulting absorbent garments have refastenable side seams and can be easily fitted to and removed from a wearer without complete removal of a wearer's clothing.

The refastenable side seams extend from a waist opening to each of two leg openings between a front panel and a back panel. Each of the refastenable side seams includes a fastening component and a mating fastening component, each of which comprises either a hook material or a loop material. A portion of the mating fastening component can be die-cut in a sinusoidal or other nesting shape, to allow the mating fastening component to be bonded to the garment after the mating fastening component is folded.

The resulting refastenable seams can be lap seams, dual fastened lap seams, standing butt seams, or dual fastened standing butt seams.

With the foregoing in mind, it is a feature and advantage of the invention to provide a pant-like absorbent garment that can be easily applied to and easily removed from a wearer without the need to entirely remove the wearer's clothing.

DEFINITIONS

Within the context of this specification, each term or phrase below will include the following meaning or meanings.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Connected" refers to the joining, adhering, bonding, attaching, or the like, of two elements. Two elements will be considered to be connected together when they are connected directly to one another or indirectly to one another, such as when each is directly connected to intermediate elements.

"Cross direction" refers to the width of a fabric in a direction generally perpendicular to the direction in which it is produced, as opposed to "machine direction" which refers to the length of a fabric in the direction in which it is produced.

Figure 3:
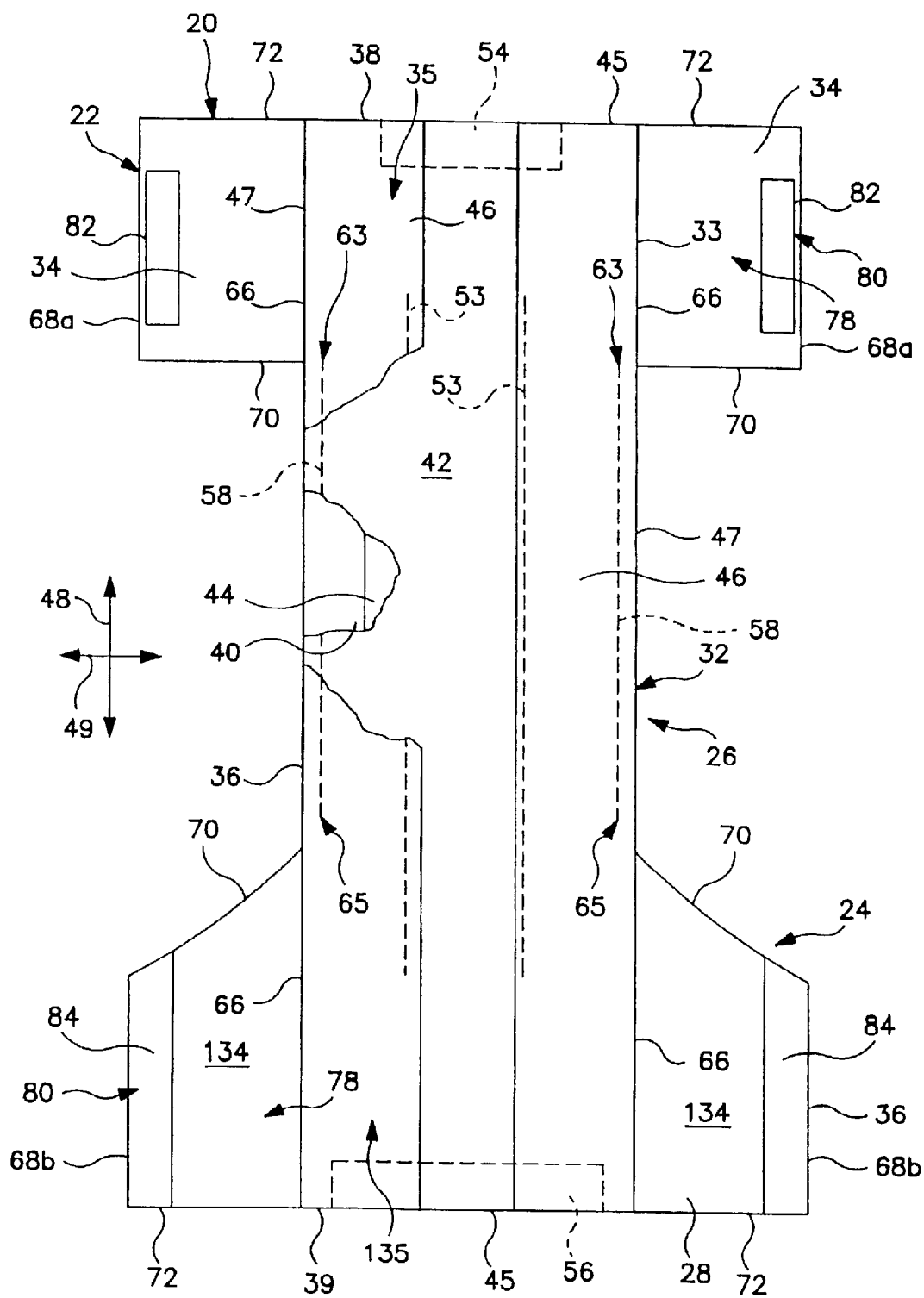
FIG. 3 is a plan view of the absorbent garment of FIGS. 1 and 2 in a partially disassembled, stretched flat state, and showing the surface of the article that faces the wearer when the article is worn, and with portions cut away to show the underlying features.

"Cross direction assembly" refers to a process in which disposable absorbent products are manufactured in an orientation in which the products are connected side-to-side, in the transverse direction shown by arrow 49 in FIG. 3, a process utilizing a cross direction assembly entails products traveling through a converting machine parallel to the direction of arrow 49, as opposed to "machine direction assembly" in which the products are connected end-to-end or waist-to-waist.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least 25 percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Fabrics" is used to refer to all of the woven, knitted and nonwoven fibrous webs.

"Film" refers to a thermoplastic film made using a film extrusion and/or foaming process, such as a cast film or blown film extrusion process. The term includes apertured films, slit films, and other porous films which constitute liquid transfer films, as well as films which do not transfer liquid.

"Flexible" refers to materials which are compliant and which will readily conform to the general shape and contours of the wearer's body.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Integral" or "integrally" is used to refer to various portions of a single unitary element rather than separate structures bonded to or placed with or placed near one another.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid impermeable" when used herein.

"Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

"Longitudinal" and "transverse" have their customary meaning, as indicated by the longitudinal and transverse axes depicted in FIG. 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Machine direction" refers to the length of a fabric in the direction in which it is produced, as opposed to "cross direction" which refers to the width of a fabric in a direction generally perpendicular to the machine direction.

"Machine direction assembly" refers to a process in which disposable absorbent products are manufactured in an orientation in which the products are connected end-to-end or waist-to-waist, in the longitudinal direction shown by arrow 48 in FIG. 3, a process utilizing a machine direction assembly entails products traveling through a converting machine parallel to the direction of arrow 48, as opposed to "cross direction assembly" in which the products are connected side-to-side.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Peel force" and "peel strain" refer to forces that tend to pull two adjoining bodies away from one another in opposite directions generally perpendicular to a plane in which the bodies are joined.

"Permanently bonded" refers to the joining, adhering, connecting, attaching, or the like, of two elements of an absorbent garment such that the elements tend to be and remain bonded during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture.

"Releasably attached," "releasably engaged" and variations thereofrefer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Shearing strain" refers to forces that tend to produce an opposite but parallel sliding motion between two bodies' planes.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 200% of its initial length, desirably to at least 250% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to a pant-like absorbent garment having refastenable fasteners, such as hook and loop fasteners, on the side panels for ease of removal and donning of the absorbent garment without complete removal of a wearer's clothing.

The principles of the present invention can be incorporated into any suitable disposable absorbent article. Examples of such suitable articles include diapers, training pants, feminine hygiene products, incontinence products, other personal care or health care garments, or the like. For ease of explanation, the description hereafter will be in terms of a child's training pant.

Figure 1:
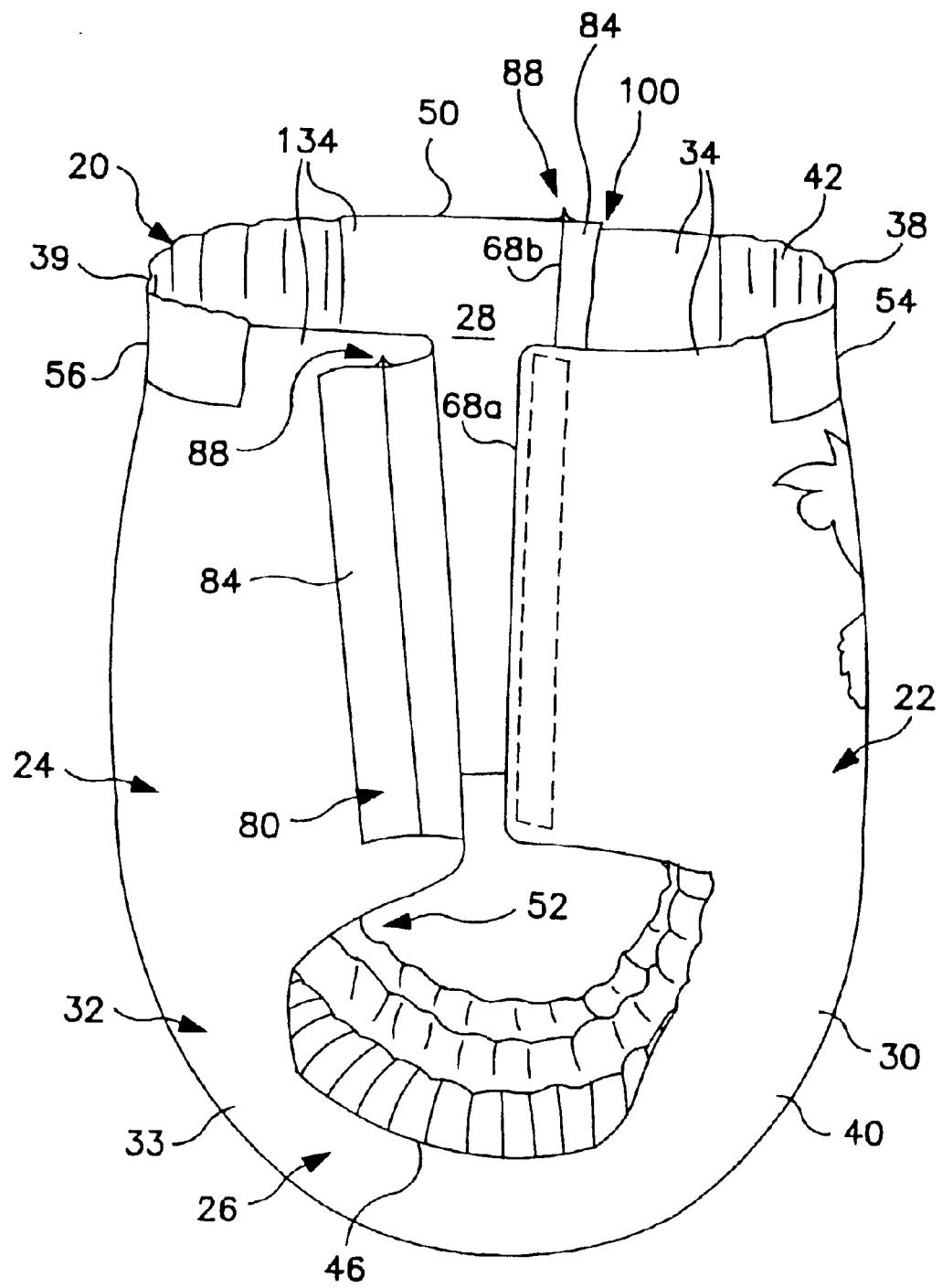
FIG. 1 is a side perspective view of an absorbent garment having refastenable sides and butt seams.

Referring to FIG. 1, a disposable absorbent article, such as a training pant 20, is illustrated in a partially fastened condition. The training pant 20 includes an absorbent chassis 32 and a fastening system 80. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39.

Figure 2:
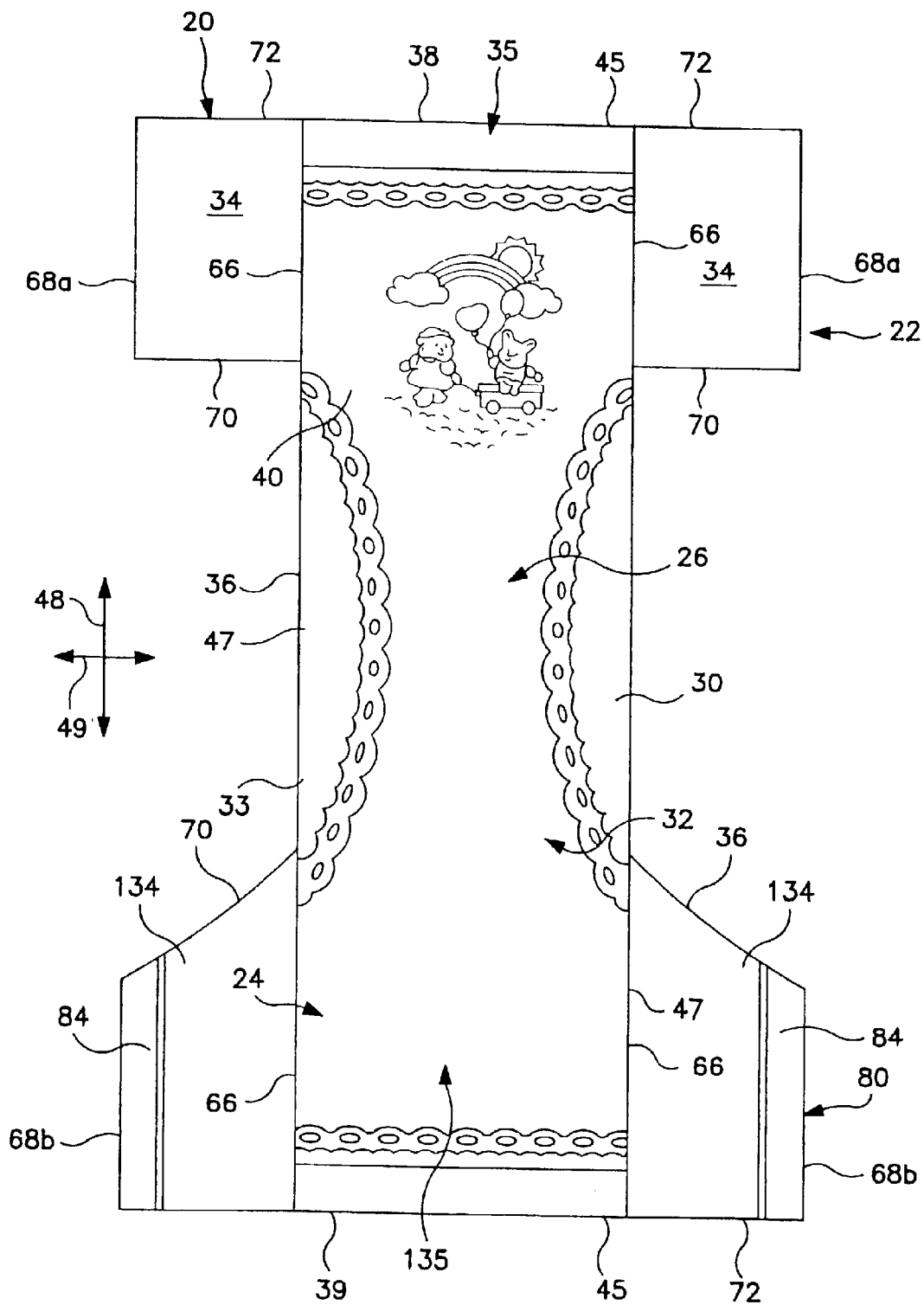
FIG. 2 is a plan view of the absorbent garment of FIG. 1 in a partially disassembled, stretched flat state, and showing the surface of the article that faces away from the wearer when the article is worn.

The illustrated absorbent chassis 32 includes a rectangular composite structure 33, a pair of transversely opposed front side panels 34, and a pair of transversely opposed back side panels 134. The composite structure 33 and side panels 34 and 134 may be integrally formed or may include two or more separate elements, as shown in FIGS. 2 and 3. The illustrated composite structure 33 includes an outer cover 40, a bodyside liner 42 which is connected to the outer cover in a superposed relation, an absorbent assembly 44 (FIG. 3) which is located between the outer cover 40 and the bodyside liner 42, and a pair of containment flaps 46 (FIG. 3). The rectangular composite structure 33 has opposite linear end edges 45 that form portions of the front and back waist edges 38 and 39, and opposite linear side edges 47 that form portions of the side edges 36 of the absorbent chassis 32 (FIGS. 2 and 3). For reference, arrows 48 and 49 depicting the orientation of the longitudinal axis and the transverse axis, respectively, of the training pant 20 are illustrated in FIGS. 2 and 3.

With the training pant 20 in the fastened position as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34 and 134 include the portions of the training pant 20 which, when worn, are positioned on the hips of the wearer.

The front region 22 of the absorbent chassis 32 includes the transversely opposed front side panels 34 and a front center panel 35 (FIGS. 2 and 3) positioned between and interconnecting the side panels, along with a front waist elastic member 54 and any other connected components. The back region 24 of the absorbent chassis 32 includes the transversely opposed back side panels 134 and a back center panel 135 (FIGS. 2 and 3) positioned between and interconnecting the side panels, as well as a rear waist elastic member 56 and any other connected components. The waist edges 38 and 39 of the absorbent chassis 32 are configured to encircle the waist of the wearer when worn and provide the waist opening 50 which defines a waist perimeter dimension. Portions of the transversely opposed side edges 36 in the crotch region 26 generally define the leg openings 52.

The absorbent chassis 32 is configured to contain and/or absorb any body exudates discharged from the wearer. For example, the absorbent chassis 32 desirably although not necessarily includes the pair of containment flaps 46 which are configured to provide a barrier to the transverse flow of body exudates. A flap elastic member 53 (FIG. 3) is operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed side edges of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 desirably includes the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39, and can extend over part or all of the waist edges. The leg elastic members 58 are desirably operatively joined to the outer cover 40 and/or bodyside liner 42 along the opposite side edges 36 and positioned in the crotch region 26 of the training pant 20. The leg elastic members 58 are desirably longitudinally aligned along each side edge 47 of the composite structure 33. Each leg elastic member 58 has a front terminal point 63 and a back terminal point 65, which points represent the longitudinal ends of the elastic gathering caused by the leg elastic members. The front terminal points 63 are desirably located adjacent the longitudinally innermost parts of the front side panels 34, and the back terminal points 65 are desirably located adjacent the longitudinally innermost parts of the back side panels 134.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads sold under the trade name LYCRA® and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impenneable. For instance, the outer cover 40 can include a liquid permeable outer layer and a liquid impermeable inner layer that are suitably joined together by a laminate adhesive (not shown). Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL° N-62 from Hodgson Textile Chemicals of Mount Holly, N.C., U.S.A. and GLUCOPON° 220UP from Henkel Corporation of Ambler, Pennsylvania, in an active ratio of 3:1. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D47805 Krefeld, Federal Republic of Germany. Typically, a superabsorbent material is capable of absorbing at least about times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 5 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34 and 134 disposed on each side of the absorbent chassis 32. These transversely opposed front side panels 34 and transversely opposed back side panels 134 can be permanently bonded to the composite structure 33 of the absorbent chassis 32 in the respective front and back regions 22 and 24, and are releasably attached to one another by a fastening system 80. More particularly, as shown best in FIGS. 2 and 3, the front side panels 34 can be permanently bonded to and extend transversely beyond the linear side edges 47 of the composite structure 33 in the front region 22 along attachment lines 66, and the back side panels 134 can be permanently bonded to and extend transversely beyond the linear side edges of the composite structure in the back region 24 along attachment lines 66. The side panels 34 and 134 may be attached using attachment means known to those skilled in the art such as adhesive, thermal or ultrasonic bonding. The side panels 34 and 134 can also be formed as a portion of a component of the composite structure 33, such as the outer cover 40 or the bodyside liner 42.

In particular embodiments for improved fit and appearance, the side panels 34 and 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34 and 134 desirably have an average length dimension of about 10 centimeters or greater, such as about 15 centimeters. While each of the side panels 34 and 134 extend from the waist opening 50 to one of the leg openings 52, the back side panels 134 have a continually decreasing length dimension moving from the attachment line 66 to a distal edge 68*b* of the back panel 134, as is best shown in FIGS. 2 and 3.

Each of the side panels 34 and 134 can include one or more individual, distinct pieces of material. In particular embodiments, for example, each side panel 34 and 134 can include first and second side panel portions that are joined at a seam, with at least one of the portions including an elastomeric material. Still alternatively, each individual side panel 34 and 134 can include a single piece of material which is folded over upon itself along an intermediate fold line (not shown).

The side panels 34 and 134 desirably include an elastic material capable of stretching in a direction generally parallel to the transverse axis 49 of the training pant 20. In particular embodiments, the front and back side panels 34 and 134 may each include an interior portion 78 disposed between the distal edge 68*a*, 68*b* and the respective front or back center panel 35 or 135. In the illustrated embodiment in FIG. 3, the interior portions 78 are disposed between the distal edges 68*a*, 68*b* and the side edges 47 of the rectangular composite structure 33. The elastic material of the side panels 34 and 134 can be disposed in the interior portions 78 to render the side panels elastomeric in a direction generally parallel to the transverse axis 49. Most desirably, each side panel 34 and 134 is elastomeric from a waist end edge 72 to a leg end edge 70. More specifically, individual samples of side panel material, taken between the waist end edge 72 and the leg end edge 70 parallel to the transverse axis 49 and having a length from the attachment line 66 to the distal edge 68*a*, 68*b* and a width of about 2 centimeters, are all elastomeric.

Suitable elastic materials, as well as one described process of incorporating elastic side panels into a training pant, are described in the following U.S. Pat. Nos. 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

The training pant 20 according to the present invention also includes a fastening system 80 for securing the training pant about the waist of the wearer (FIG. 1). The illustrated fastening system 80 includes fastening components 82 that are adapted to refastenably connect to mating fastening components 84. In one embodiment, one surface of each of the fastening components 82 and 84 includes a plurality of engaging elements that project from that surface. The engaging elements of these fastening components 82 are adapted to repeatedly engage and disengage the engaging elements of the mating fastening components 84.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. The fastening components 82 and the mating fastening components 84 are desirably rectangular, although they may alternatively be square, round, oval, curved or otherwise non-rectangularly shaped.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. The term "resilient" as used herein refers to an interlocking material having a predetermined shape and the property of the interlocking material to resume the predetermined shape after being engaged and disengaged from a mating, complementary interlocking material. Suitable hook material can be molded or extruded of nylon, polypropylene or another suitable material. Suitable single-sided hook materials for the fastening components 82 or the mating fastening components 84 are available from Velcro Industries B.V., Amsterdam, Netherlands or affiliates thereof, and are identified as Velcro HTH-829 with a uni-directional hook pattern and having a thickness of about 0.089 millimeters (3.5 mils) and HTH-851 with a uni-directional hook pattern and having a thickness of about 0.051 millimeters (2 mils).

Figure 4:
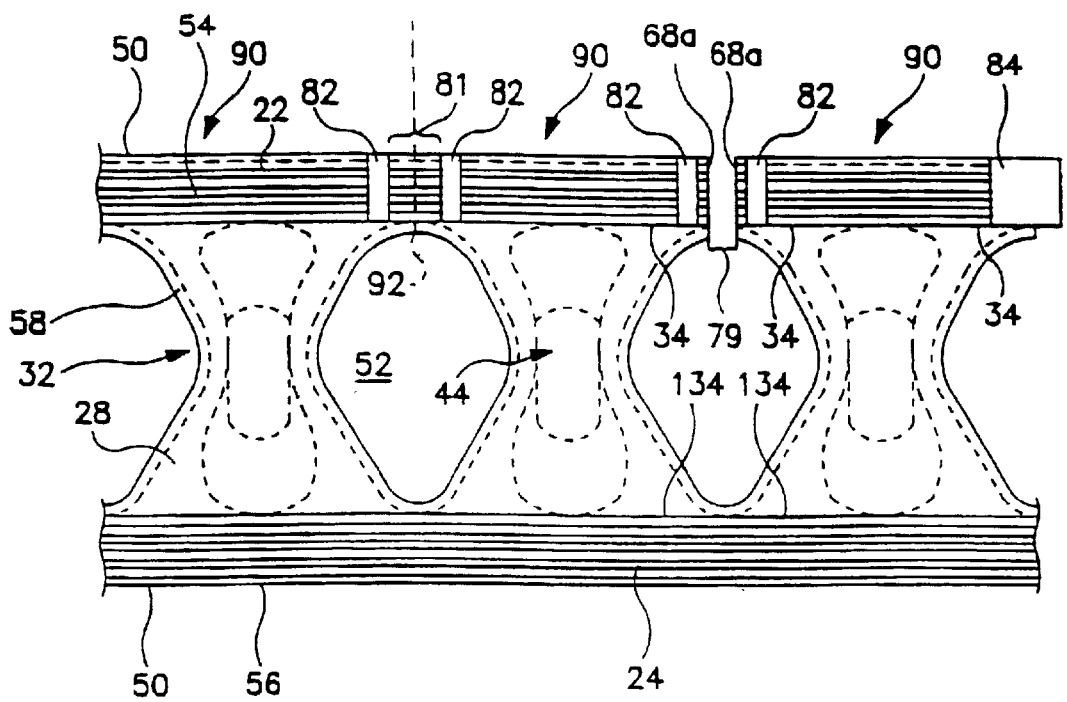
FIG. 4 is a plan view of a cross direction assembly for producing one embodiment of the invention.

With particular reference to FIG. 4, a plurality of garment assemblies 90 aligned in a cross direction for producing one embodiment of the invention is shown. The garment assembly 90 includes a lamination of films and nonwovens, including a bodyside liner 42 and an outer cover 40, together with waist elastics 54 and 56, leg elastics 58, and an absorbent assembly 44, as described above, placed on a vacuum device (not shown). Adjacent garment assemblies 90 are joined between the back side panel 134 and the front side panel 34. The exposed surface of the garment assembly 90 is the inner surface 28 of the chassis 32. One method of attaching the fastening components 82 and the mating fastening components 84 to the absorbent garment 20, resulting in a garment 20 in accordance with the present invention, involves placing the fastening components 82 on the front region 22 near the planned locations of the distal edges 68*a*, with a spacing 81 of roughly 0.25–1.0 inch between fastening components 82 on adjacent garment assemblies 90. The fastening components 82 can be bonded to the front region 22 with ultrasonic, thermal, or adhesive bonds, or other means. Adjacent garment assemblies 90 are then separated at the front side panels 34 by cutting along dotted line 92 from the waist 50 to the leg opening 52 (FIG. 4) between adjacent fastening components 82. When the assemblies 90 are cut, the elastic property of the front side panels 34 causes the front side panels 34 to snap back from the cutting line 92 to the fastening components 82, creating a gap 79. Alternatively, a section of the adjoining front side panels 34 between adjacent fastening components 82 can be cut out to create the gap 79, thereby ensuring that each of the fastening components 82 is closely aligned with the corresponding resulting front distal edge 68*a*.

Figure 5:
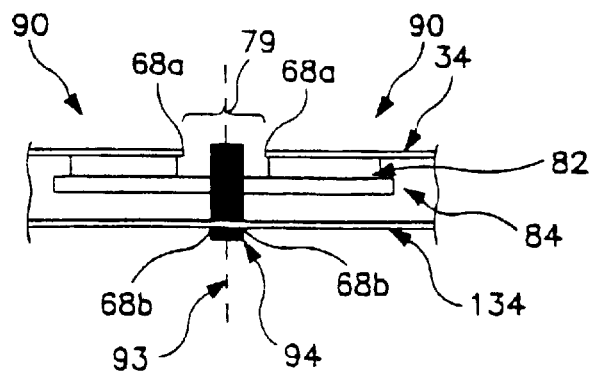
FIG. 5 is a top view of a fastening system during assembly in one embodiment of the invention.

Referring to FIG. 4, a mating fastening component 84 is placed over two of the adjacent fastening components 82, thereby covering the gap 79 with the mating fastening component 84 and joining the front side panels 34 of the adjacent assemblies 90 together again. The garment assemblies 90 are then removed from the vacuum device, folded longitudinally and bonded such that adjacent back side panels 134 and/or adjacent rear elastic bands 56 are bonded to the mating fastening component 84, at bonding seam 94, as shown in FIG. 5, between the adjacent fastening components 82, and further in the gap 79 between the distal edges 68*a*. The bonding seam 94 must not attach the distal edge 68*a* to the fastening component 84.

Adjacent back side panels 134 are then cut through the bonding seam 94, and the mating fastening components 84 are severed into two halves, along cut line 93 shown in FIG. 5, thereby separating adjacent garment assemblies 90 from one another. Each resulting garment 20 has a fastening component 82 near each distal edge 68*a* of front elastic members 54 and a mating fastening component 84 (constituting one-half of an original component 84) attached along each distal edge 68*b*, as shown in FIG. 6.

Figure 6:
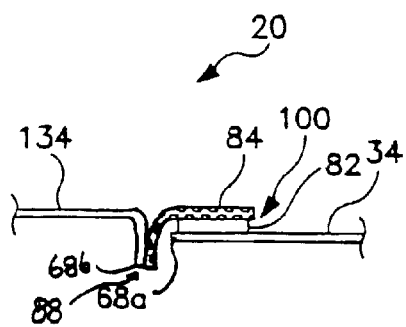
FIG. 6 is a top view of a fastening system of a completed product in one embodiment of the invention.

A standing butt seam 88 is thereby formed between the fastening component 84 and the back side panel 134, as shown in FIGS. 1 and 6. As used herein, the term "standing butt seam" refers to a seam wherein two separate pieces of substrate are bonded together face-to-face or back-to-back in close proximity to an outer edge of each of the pieces of substrate, and the outer edges of the pieces of substrate project outward from the finished product, placing the seam 88 in peel, as opposed to shearing strain.

The resulting absorbent garment 20, shown in FIG. 1, has refastenable, prefastened hook and loop fasteners, oriented as lap side seams 100, along the distal edges 68*a* and 68*b* of the front and back side panels 34 and 134. The resulting orientation puts the prefastened seams 100 under shearing strain during use, as opposed to peel forces. The term "lap side seam," as used herein, refers to a seam connecting the front and back side panels 34 and 134 or materials bonded thereto, such as fastening components 82 and 84, such that the front and back side panels and/or materials bonded thereto overlap and the seam is located between the distal edges 68*a* and 68*b* of the front and back side panels 34 and 134. The refastenable lap side seams experience a shearing strain during use, as opposed to peel forces, thereby reducing the likelihood of the seams opening unexpectedly.

Figure 7:
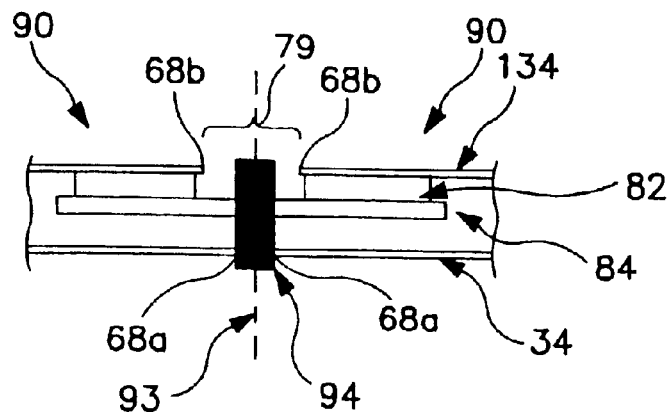
FIG. 7 is a top view of a fastening system during assembly in one embodiment of the invention.

An alternative embodiment of the present invention, similar to the previous embodiment, can be produced by bonding the fastening components 82 to the back region 24 near the planned locations of the distal edges 68*b*, instead of to the front region 22. This method is further carried out by cutting between adjacent back side panels 134, placing a mating fastening component 84 over two adjacent fastening components 82, thereby covering the gap 79 with the mating fastening component 84 and joining the adjacent back side panels 134 together again. The garment assemblies 90 are then removed from the vacuum device, folded longitudinally and bonded such that adjacent front side panels 34 and/or adjacent front elastic bands 54 are bonded, as shown in FIG. 7, to the mating fastening component at the bonding seam 94 on the fastening component between the adjacent fastening components 82, and further in the gap 79 between the distal edges 68*b*. A standing butt seam 88 is thereby formed between the fastening component 84 and the front side panel 34.

Figure 8:
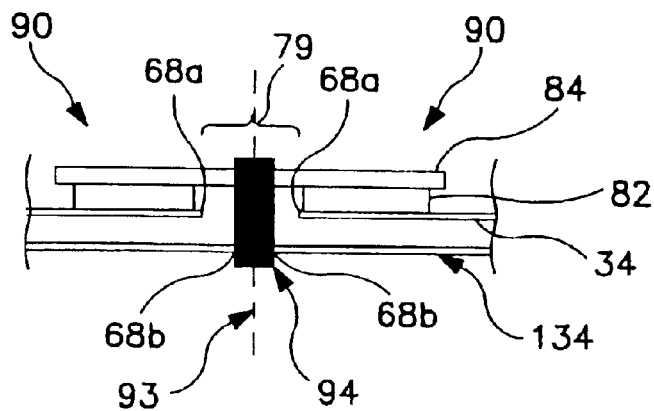
FIG. 8 is a top view of a fastening system during assembly in one embodiment of the invention.
Figure 9:
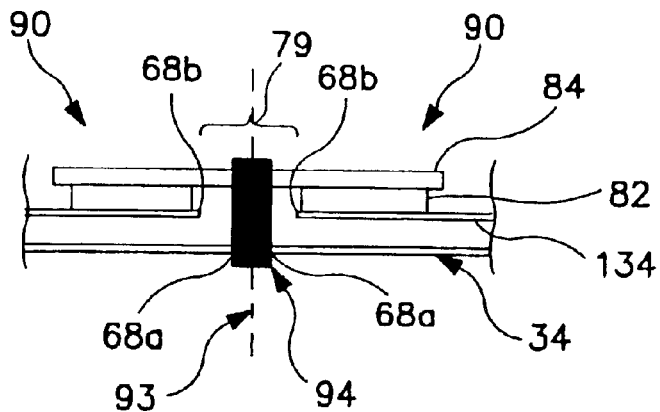
FIG. 9 is a top view of a fastening system during assembly in one embodiment of the invention.

Yet another alternative embodiment of the present invention can be produced by following the same assembly procedure as illustrated in FIG. 4, but instead of bonding the fastening components 82 to the inner surface 28 of the chassis 32, the outer surface 30 is exposed and the fastening components 82 are bonded thereto. Furthermore, the fastening components 82 can be bonded either to the front region 22 near the planned locations of the distal edges 68*a*, as shown in FIG. 8, or to the back region 24 near the planned locations of the distal edges 68*b*, as shown in FIG. 9. As in the assembly procedure described in relation to FIG. 4, the garment assemblies 90 are removed from the vacuum device, folded longitudinally and bonded such that the adjacent back side panels 134 and/or adjacent rear elastic bands 56 are bonded, as shown in FIG. 8, to the mating fastening component 84, or folded in the same manner and bonded such that the adjacent front side panels 34 and/or adjacent front elastic bands 54 are bonded, as shown in FIG. 9.

Figure 10:
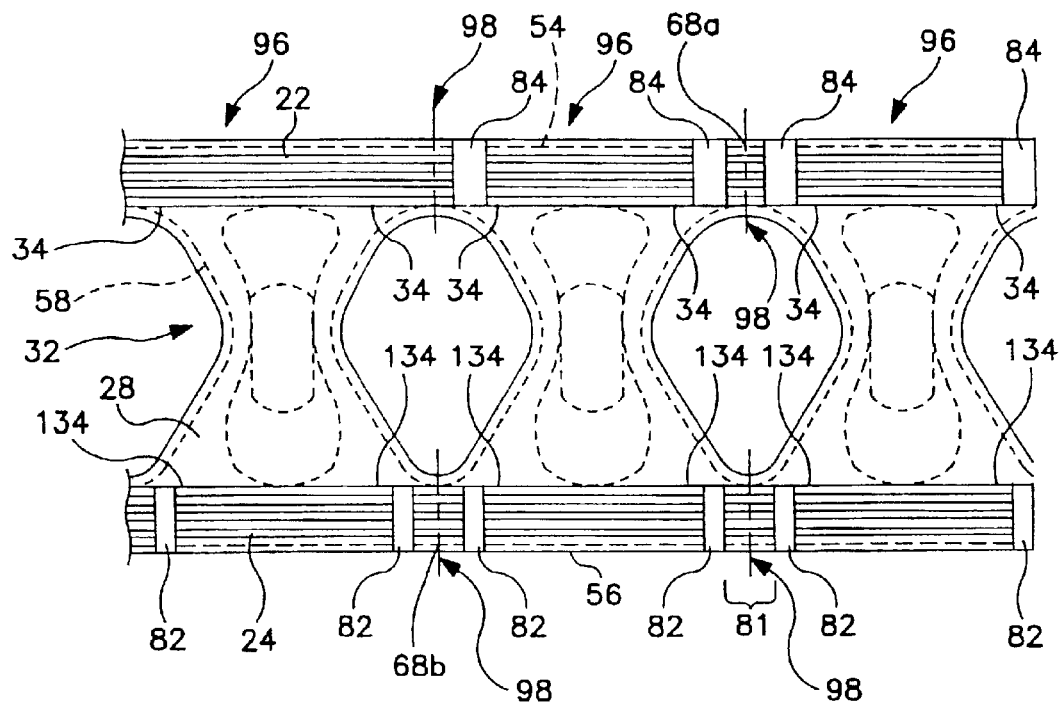
FIG. 10 is a plan view of a cross direction assembly for producing another embodiment of the invention.

An alternative method for producing absorbent garments 20 with lap side seams 100 is similar to the method described above. More particularly, this method includes a plurality of garment assemblies 96 aligned in a cross direction, as shown in FIG. 10. The cross direction garment assembly 96 is similar to the cross direction garment assembly 90 in FIG. 4. To create lap seams 100 (shown in FIGS. 11 and 15), first the fastening components 82 are placed on the back region 24, more specifically on the elastic band 56 region of back side panels 134, near the planned locations of the distal edges 68*b*, with a spacing 81 of roughly 0.25–1.0 inch between fastening components 82 on adjacent garment assemblies 96. Alternatively, a single, oversized fastening component can be placed on the back region 24 of two adjacent garment assemblies 96, to be separated at the product cut-off stage. Two mating fastening components 84 are folded once, i.e. C-folded, cut to length, and placed on the inner surface 28 of the front region 22, more specifically on the elastic band 54 region of front side panels 34, near the planned locations of the distal edges 68*a*, with a spacing 81 of roughly 0.25–1.0 inch between mating fastening components 84 on adjacent garment assemblies 96, with the folded edges 97 facing one another across a cut line 98, as shown in FIG. 12. The folded mating fastening components 84 are attached to the front region 22 with adhesive or can be ultrasonically bonded to the front region 22 along one edge if the fold is not completely symmetrical.

The garment assemblies 96 are then folded longitudinally, which aligns the fastening components 82 with the folded mating fastening components 84. Adjacent garment assemblies 96 are then separated along cut line 98, as shown in FIG. 12, thereby forming discrete products having a pair of refastenable, prefastened hook and look fasteners with lap side seams 100.

Figure 12:
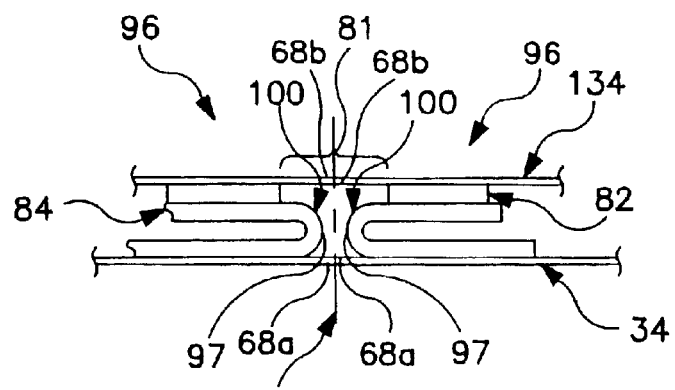
FIG. 12 is a top view of a fastening system during assembly in one embodiment of the invention.
Figure 13:
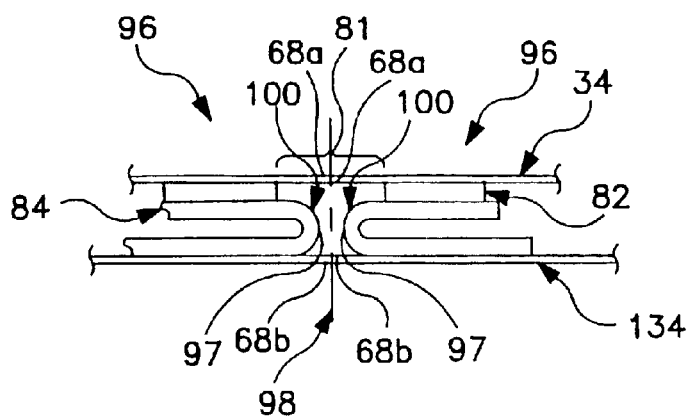
FIG. 13 is a top view of a fastening system during assembly in one embodiment of the invention.

FIG. 13, similar to FIG. 12, shows that the fastening components 82 can be bonded to the elastic band 54 region of front side panels 34, near the planned locations of the distal edges 68a, instead of to the back side panels 134, and that the mating fastening components 84 can be bonded to the elastic band 56 region of the back side panels 134, near the planned locations of the distal edges 68b, instead of to the front side panels 34.

Figure 14:
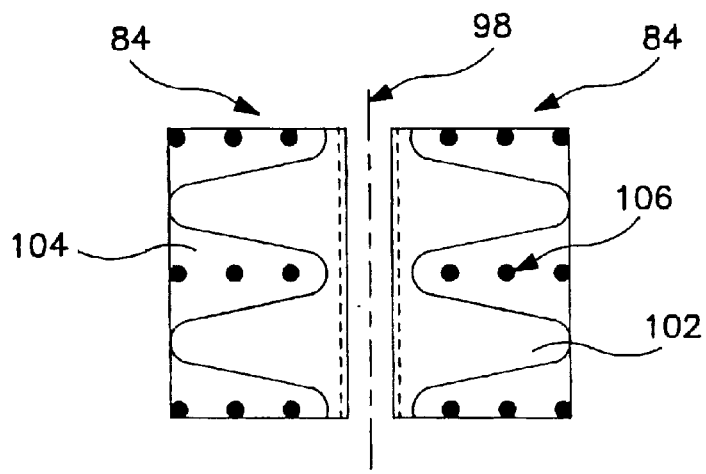
FIG. 14 is a front view of a fastening system during assembly in yet another embodiment of the invention.
Figure 15:
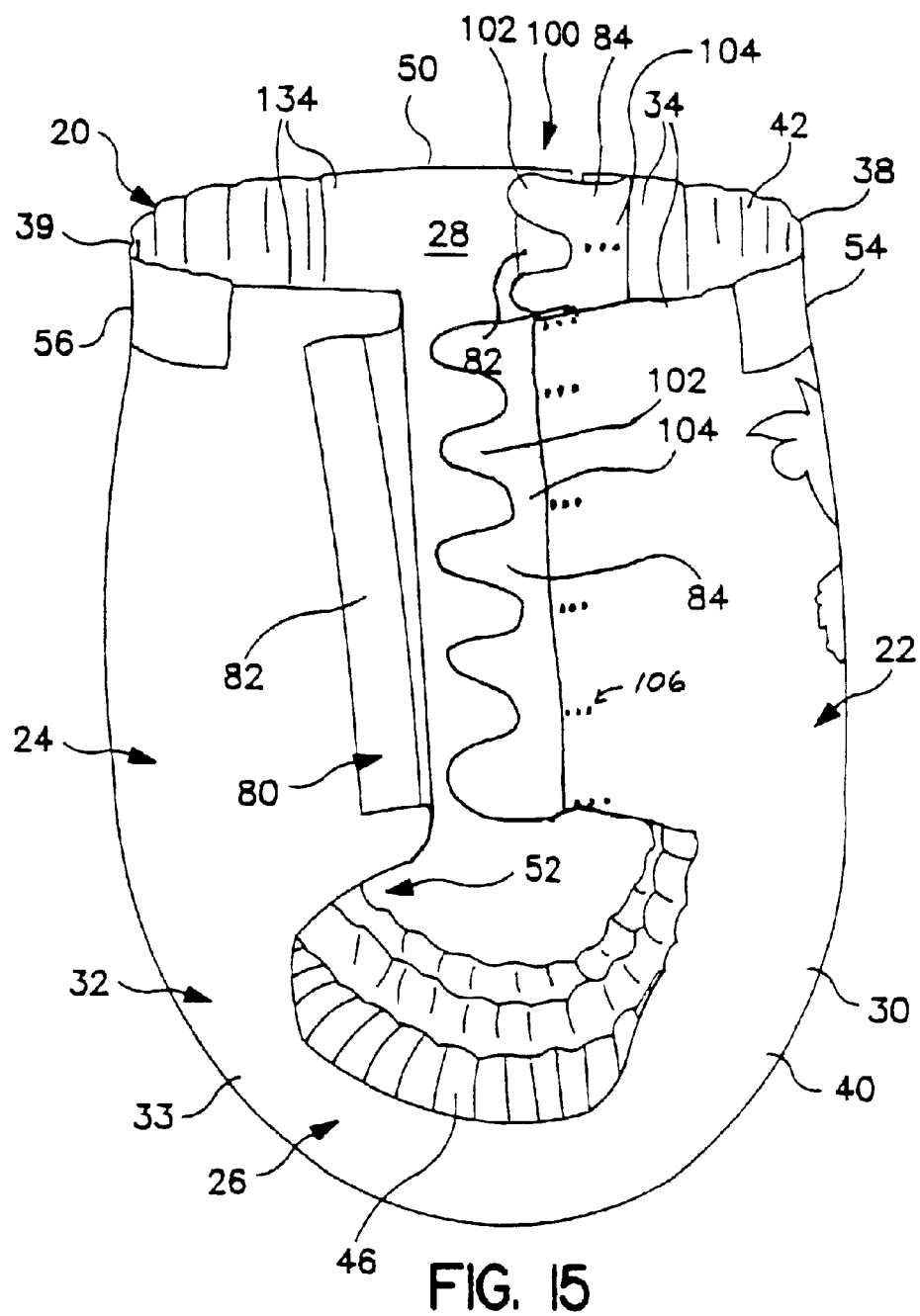
FIG. 15 is a side perspective view of an absorbent garment having refastenable lap side seams.

Referring to FIG. 14, in a further embodiment of the present invention, the fastening components 82 and the mating fastening components 84 are attached to the garment assembly 96 according to the method described above for producing a garment 20 having refastenable, prefastened hook and loop fasteners with lap side seams; however, the mating fastening components 84 have a die-cut portion 102 and an uncut portion 104. The die-cut portion 102 is a sinusoidal shape, or other shape that preferably can be nested. The uncut portion 104 is the portion bonded to either the front side panel 34 or the back side panel 134, thereby not constraining the die-cut portion 102. FIG. 14 is a top view of the fasteners shown in FIG. 12, further showing the die-cut portions 102 of the mating fastening components 84 and the points 106 at which the uncut portions 104 are bonded to the front side panel 34. FIG. 15 is a side perspective view of a partially fastened absorbent product 20 having the lap side seams 100 illustrated in FIGS. 11, 12 and 14.

Yet another embodiment of the present invention is an absorbent garment 20 having a refastenable, dual prefastened hook and loop fastener with lap side seams. More specifically, this embodiment has a fastener in both the front and the back on each side of the garment 20. This embodiment can be produced in either a cross direction process (FIG. 16) or a machine direction process (FIG. 17). Preferably, equal widths of fastening material 82 and 84 are used in the front and the back of the garment 20.

Figure 11:
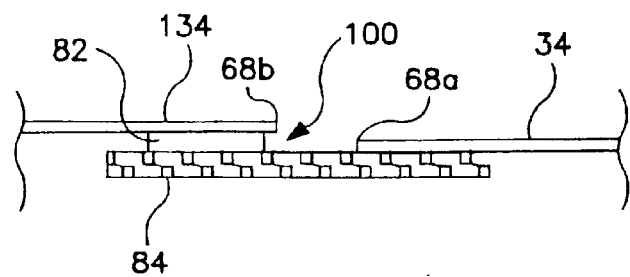
FIG. 11 is a top view of a fastening system of a completed product in one embodiment of the invention.
Figure 16:
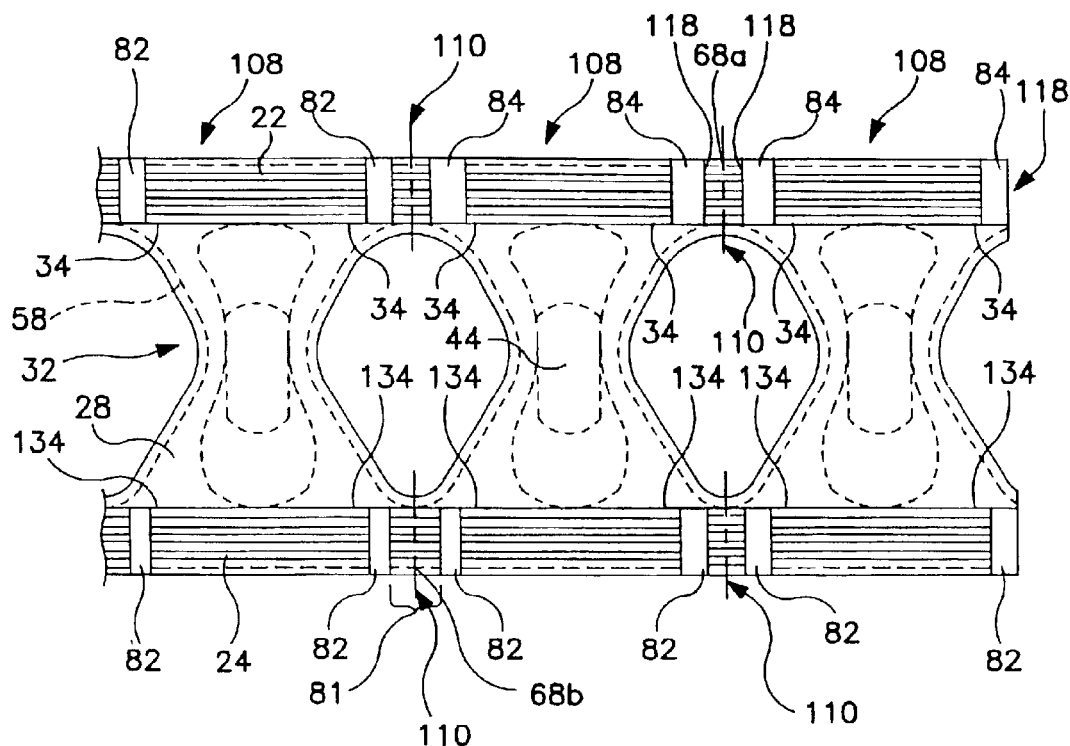
FIG. 16 is a plan view of a cross direction assembly for producing an embodiment of the invention having dual lap seams.
Figure 17:
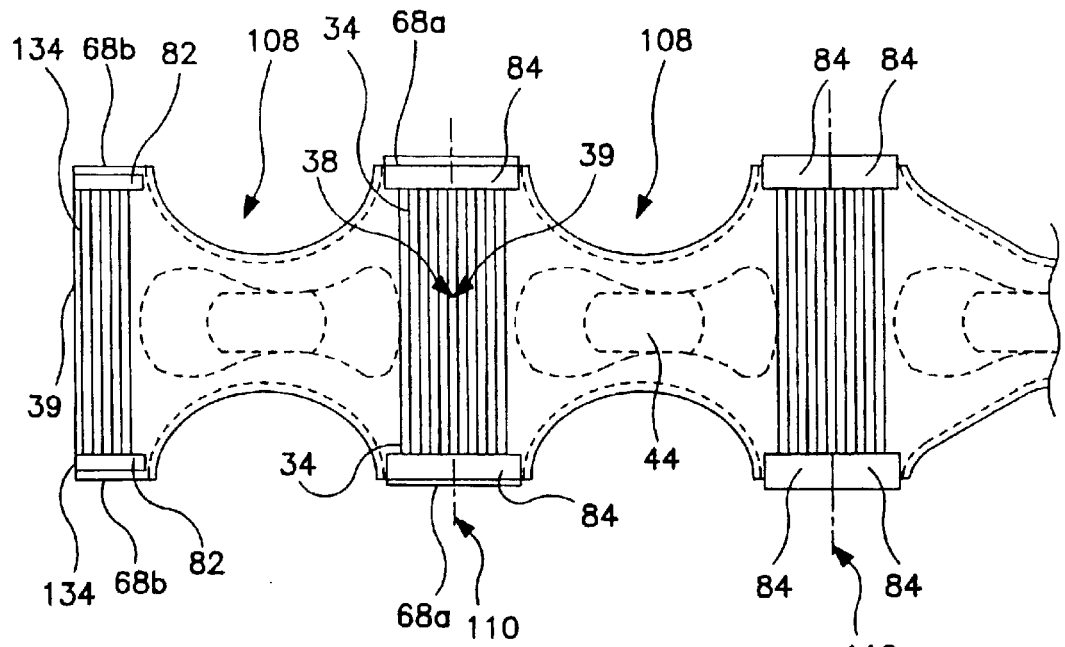
FIG. 17 is a plan view of a machine direction assembly for producing an embodiment of the invention having dual lap seams.

Referring to FIGS. 16 and 17, methods for producing this embodiment are similar to the methods described above for producing a garment with lap side seams 100 (FIGS. 1, 6, 11). In these methods, four pieces of fastening component 82 are bonded to each product near the planned locations of distal edges 68a and 68b, with a spacing 81 of roughly 0.25–1.0 inch between fastening components 82 on adjacent garment assemblies 108 in the cross direction process (FIG. 16). Alternatively, in the cross direction process (FIG. 16) a single, oversized fastening component can be placed overlapping the planned locations of the distal edges 68a and 68b of two adjacent assemblies, to be separated at the product cut-off stage. Likewise, in the machine direction process (FIG. 17), a single, oversized fastening component can be placed overlapping the planned locations of the front waist edge 38 and the back waist edge 39 of adjacent assemblies 108, to be separated at the product cut-off stage. Two mating fastening components 84 are folded once, i.e. C-folded, cut to length, and placed on the inner surface 28 of the front side panels 34, or back side panels 134, near the planned locations of the distal edges 68a or 68b, also with a spacing 81 of roughly 0.25–1.0 inch between mating fastening components 84 on adjacent garment assemblies 108 in the cross direction process (FIG. 16), with the folded edges 118 facing one another, as shown in FIG. 18.

Figure 18:
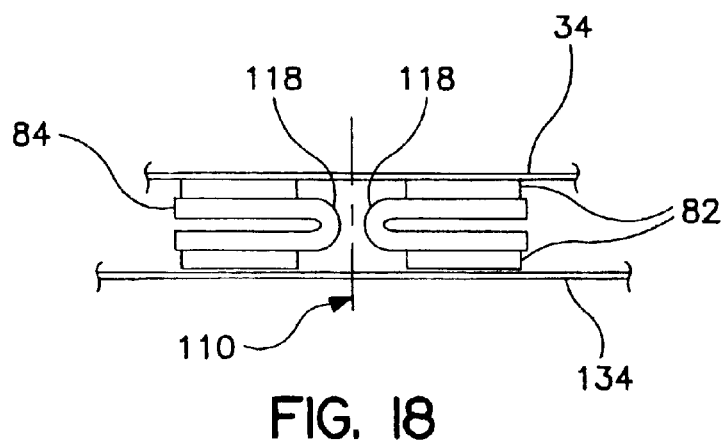
FIG. 18 is a top view of a fastening system during assembly in an embodiment of the invention having dual lap seams.
Figure 19:
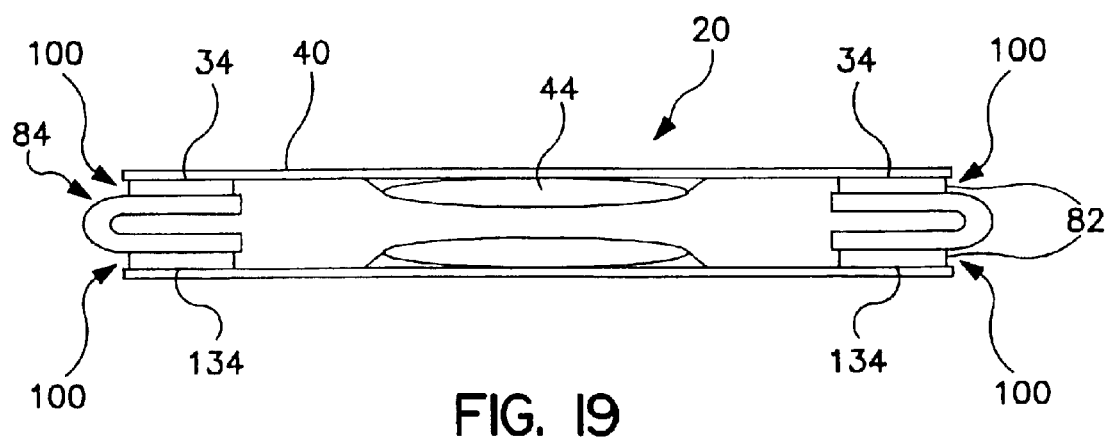
FIG. 19 is a top view of an absorbent garment having dual lap seams.

In the cross direction process (FIG. 16), the garment assemblies 108 are then folded longitudinally, which aligns the fastening components 82 with the folded mating fastening components 84, as shown in FIG. 18. Adjacent garment assemblies 108 are then separated along cut line 110, thereby forming discrete products with dual lap side seams 100, as shown in FIG. 19. A cross-sectional view of a finished absorbent garment 20, showing a similar perspective as shown in FIG. 18, is shown in FIG. 19. The mating fastening components 84 can be unfastened and refastened on either the front side of the garment or the back side of the garment 20.

Figure 20:
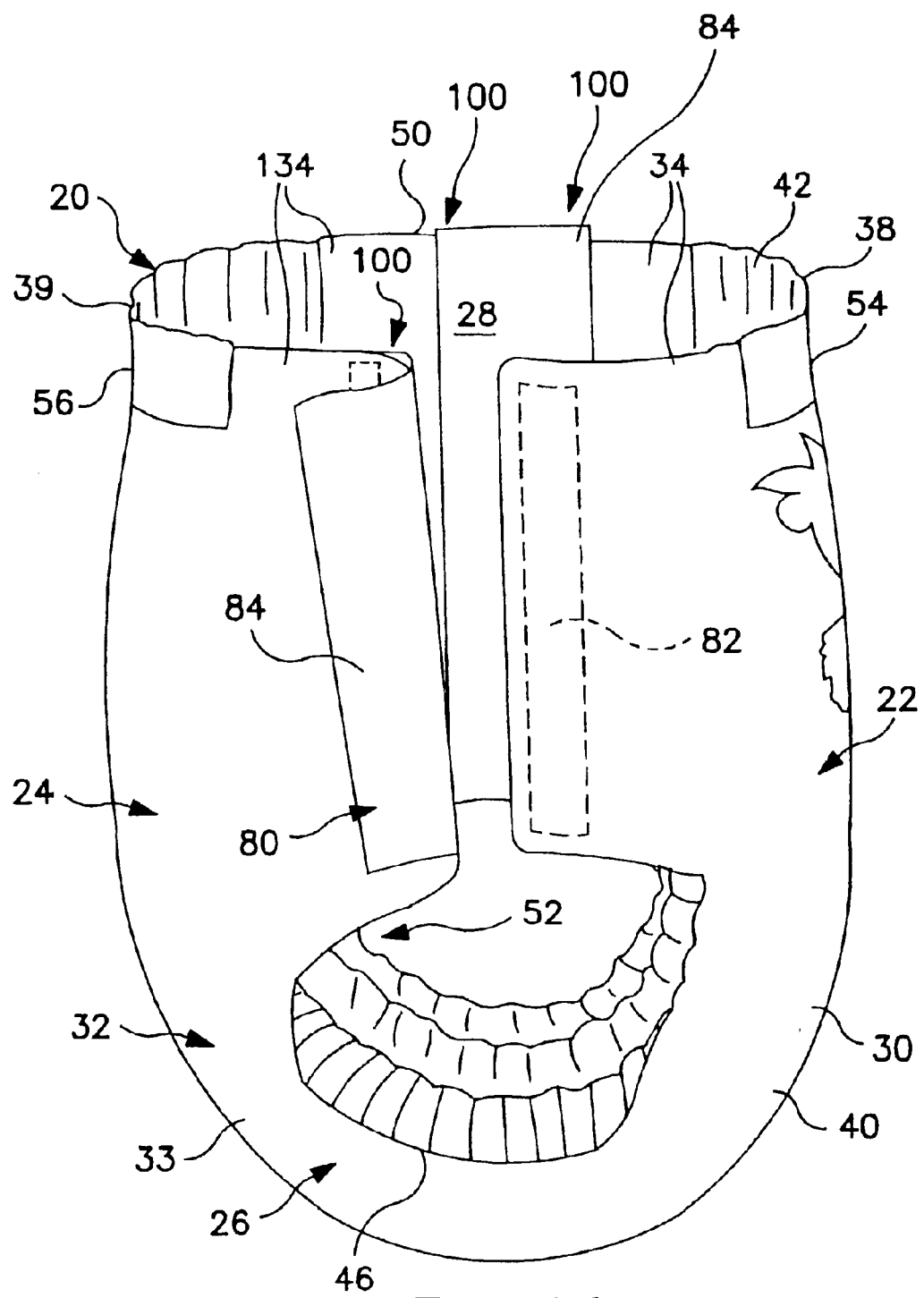
FIG. 20 is a side perspective view of an absorbent garment having dual refastenable lap seams.

In the machine direction process (FIG. 17), adjacent assemblies 108 are first separated at the planned locations of the front waist edge 38 and the back waist edge 39 of adjacent assemblies. Then, each individual assembly 108 is folded longitudinally, thereby aligning the fastening components 82 with the folded mating fastening components 84, as shown in FIG. 19. FIG. 20 is a side perspective view of a partially fastened absorbent product 20 having the lap side seams 100 illustrated in FIG. 19.

Yet another embodiment of the present invention is an absorbent garment 20 having refastenable, dual prefastened hook and loop fasteners with standing butt seams and dual lap side seams. Like the previous embodiment, this embodiment can be produced in either a cross direction process (FIG. 21) or a machine direction process (FIG. 22).

Figure 21:
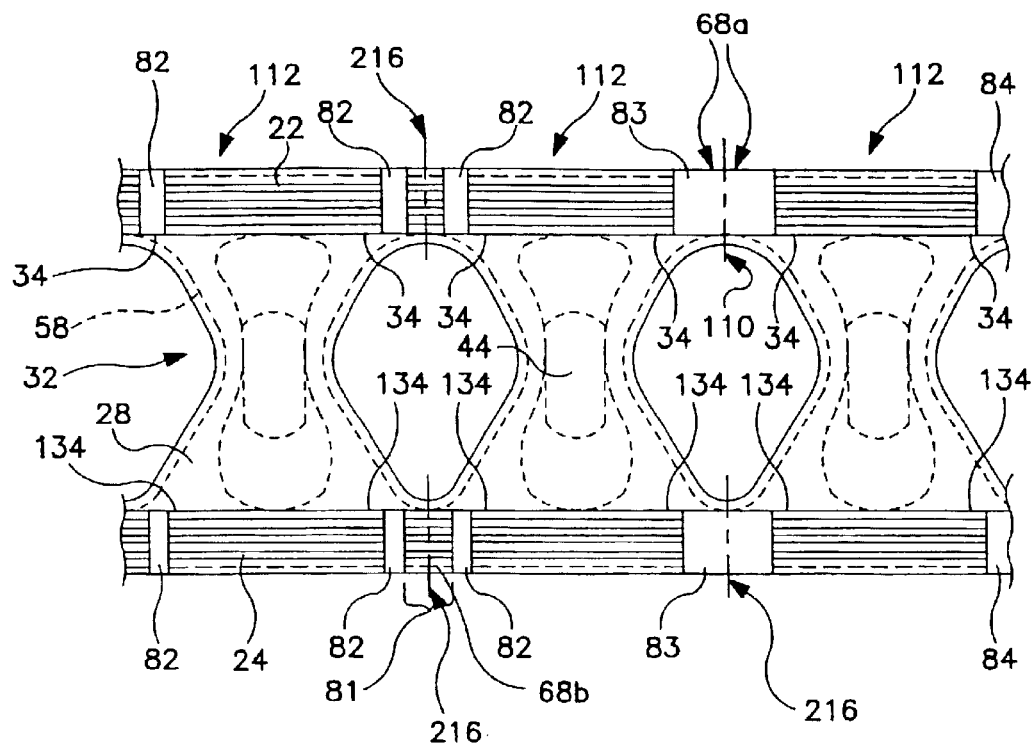
FIG. 21 is a plan view of a cross direction assembly for producing an embodiment of the invention having dual refastenable sides and butt seams.
Figure 22:
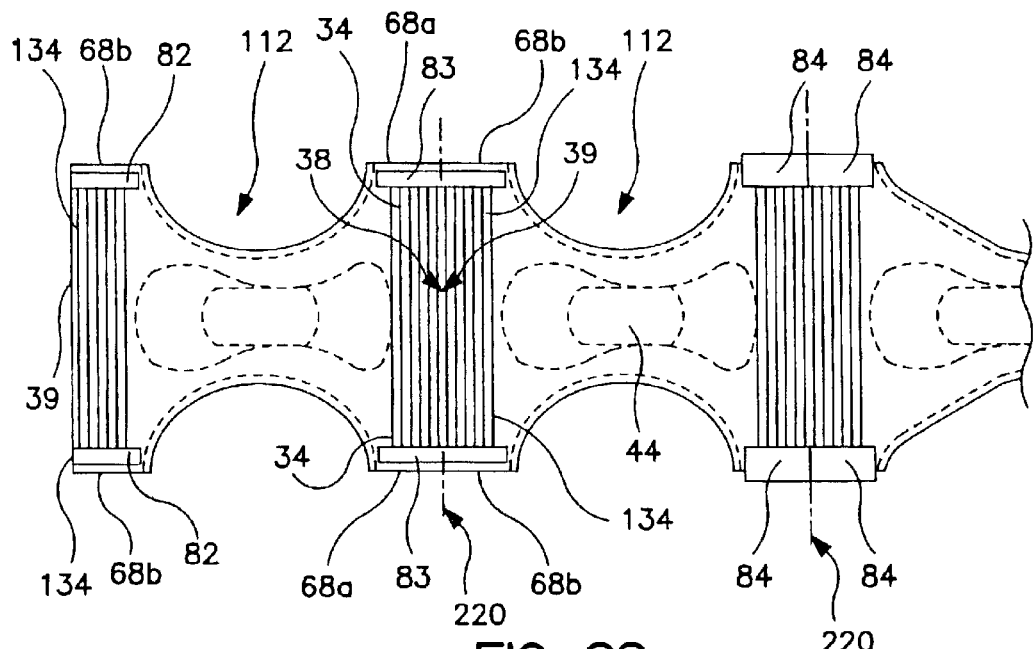
FIG. 22 is a plan view of a machine direction assembly for producing an embodiment of the invention having dual refastenable sides and butt seams.

As in the previous methods, two fastening components 82 are bonded to the back side panels 134 and two fastening components 82 are bonded to the front side panels 34 of each garment assembly 112, with a spacing 81 of roughly 0.25–1.0 inch between fastening components 82 on adjacent garments 20 in the cross direction process (FIG. 21). Alternatively, in the cross direction process (FIG. 21), a single, oversized fastening component 83 can be placed overlapping the planned locations of the distal edges 68a and 68b of two adjacent garment assemblies 112, to be separated at the product cut-off stage. Likewise, in the machine direction process (FIG. 22), two oversized strips of fastening components 83 can be applied to both the front side panel 34 and the back side panel 134 overlapping the planned locations of the front waist edge 38 and the back waist edge 39 of adjacent assemblies, to be separated at the product cut-off stage.

Figure 23:
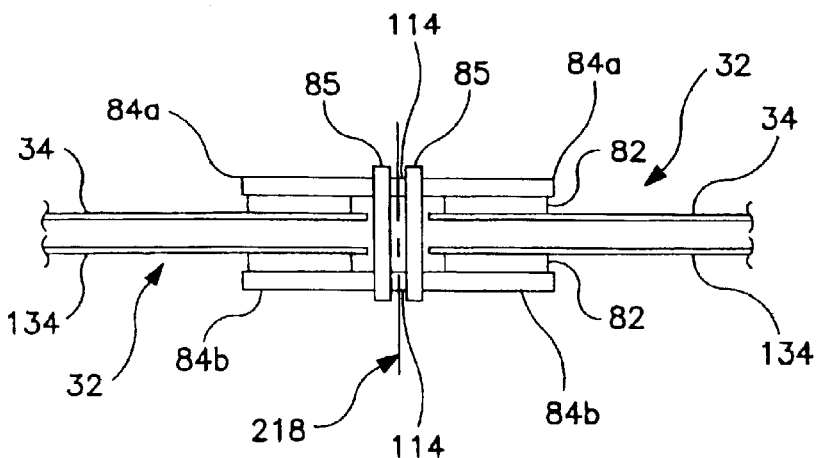
FIG. 23 is a top view of a fastening system during assembly in an embodiment of the invention having dual refastenable sides and butt seams.

After the fastening components 82 have been bonded to the garment assembly 112 in the cross direction process (FIG. 21), adjacent assemblies 112 are then separated from one another along cut line 216, and the adjacent assemblies 112 are spaced apart to provide room between the distal edges 68a and 68b of adjacent products. The gap is provided in order to prevent the chassis 32 or the fastening components 82 from being bonded together with the mating fastening components 84 when the standing butt seam 88 is formed, FIGS. 24 and 25. When the adjacent assemblies 112 are separated, the elastic property of the front side panels 34 and the back side panels 134 causes the front side panels 34 and the back side panels 134 to snap back from the cut to the fastening components 82, maintaining the gap. Alternatively, a section of the adjoining front and back side panels 34, 134 between the fastening components 82 of adjacent assemblies 112 can be cut out to maintain the aforementioned gap, thereby ensuring that each of the fastening components 82 is closely aligned with the corresponding resulting distal edge 68a, 68b. Two large patches of mating fastening components 84 are applied over the fastening components 82 of adjacent assemblies 112, thereby bridging the gap between the assemblies 112. All of the garment assemblies 112 connected by mating fastening components 84 are then folded in half lengthwise. The front mating fastening component 84a is then bonded, at bonding seam 85, to the back mating fastening component 84b along a distal edge 114 of each mating fastening component 84 outside of the chassis 32, as shown in FIG. 23. Adjacent garment assemblies 112 are then separated along cut line 218, thereby forming discrete products with standing butt seams 88, FIGS. 24 and 25.

Figure 24:
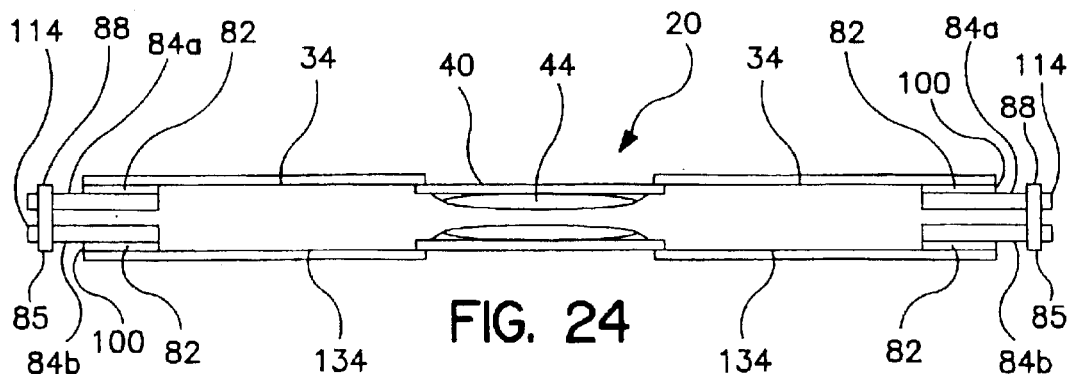
FIG. 24 is a top view of an absorbent garment having dual refastenable sides and butt seams.
Figure 25:
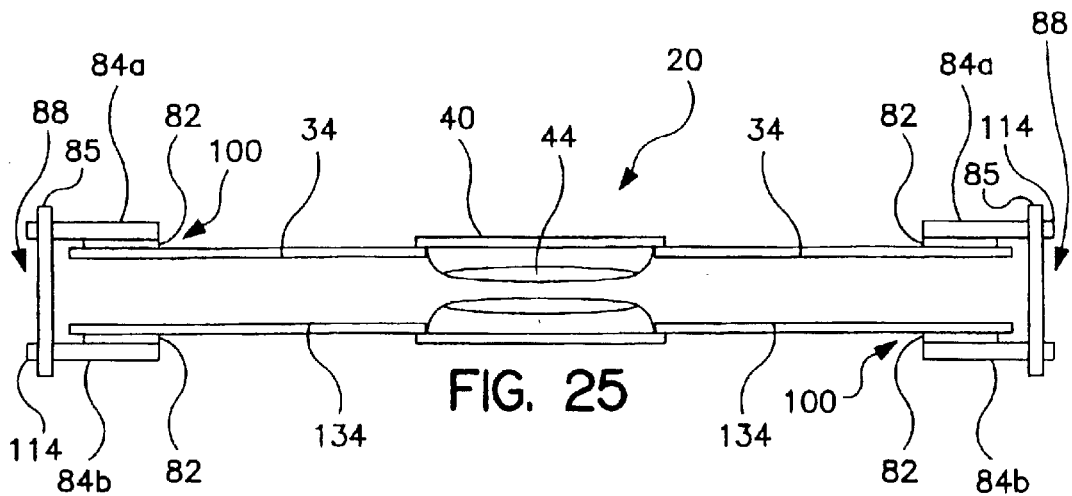
FIG. 25 is a top view of an absorbent garment having dual refastenable sides and butt seams.

After the fastening components 82 have been bonded to the garment assembly 112 in the machine direction process (FIG. 22), four mating fastening components 84, wider than the fastening components 82, are aligned with and engaged with the fastening components 82, such that the mating fastening components 84 extend beyond the distal edges 68a and 68b of the garment assemblies 112. Similar to the fastening components 82, the mating fastening components 84 can be four separate components or can alternatively extend to cover the fastening components 82 on adjacent products. The adjacent garment assemblies 112 are then separated, along cut line 220 (FIG. 22), thereby also separating any extending fastening components 82 and/or mating fastening components 84. Each garment assembly 112 is then folded longitudinally, which aligns the mating fastening components 84 back-to-back with one another on either side of the garment, as shown in FIG. 24, or front-to-front with one another, as shown in FIG. 25. The front mating fastening component 84a is then bonded to the back mating fastening component 84b along a distal edge 114 of each mating fastening component 84a and 84b outside of the chassis 32, thereby forming a standing butt seam 88.

Figure 26:
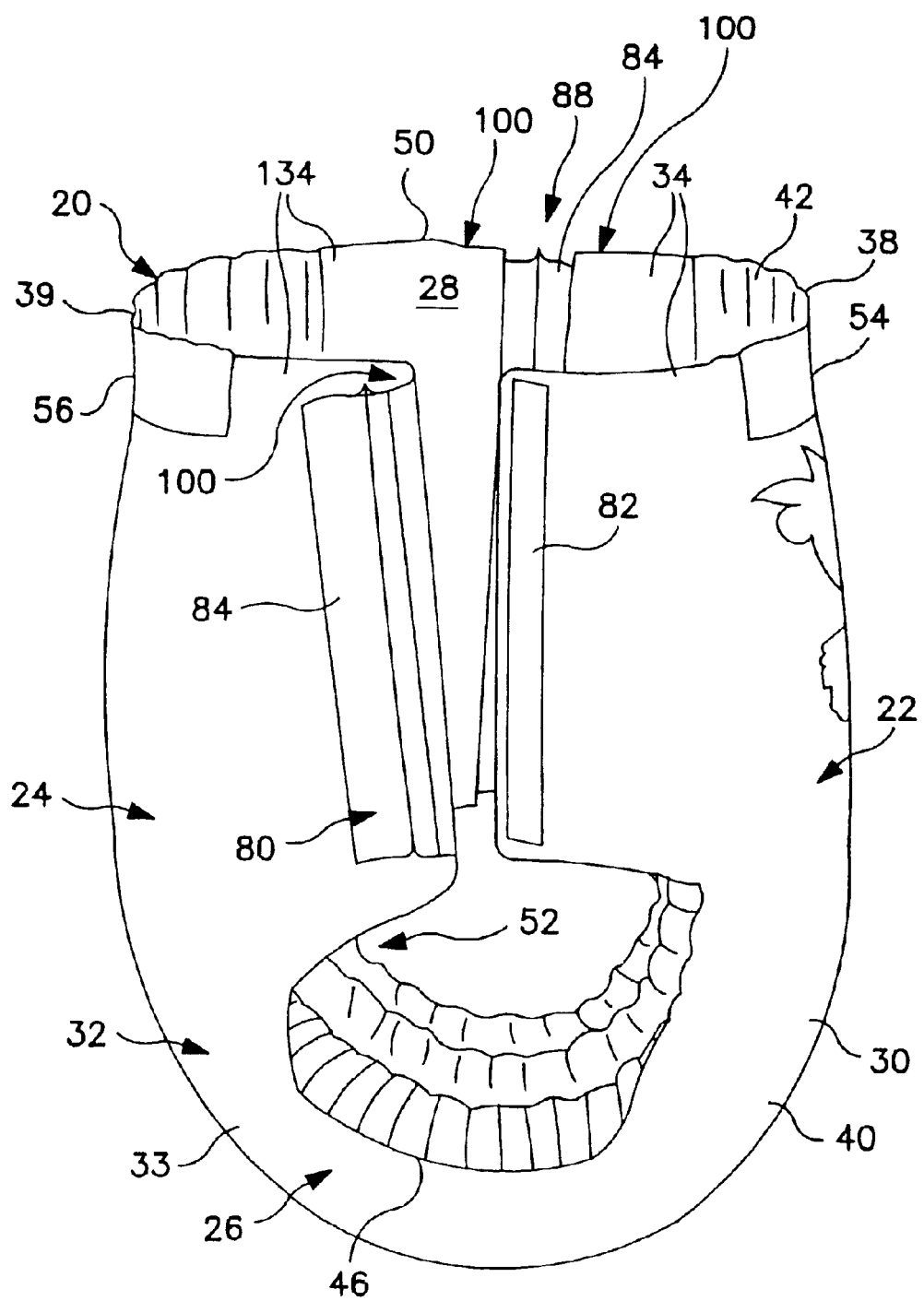
FIG. 26 is a side perspective view of an absorbent garment having dual refastenable sides and butt seams.

The assembly procedures as illustrated in FIGS. 21 and 22 can be carried out with the fastening components 82 being bonded to either the inner surface 28 or the outer surface 30 of the assembly 112. The embodiment in FIG. 24 shows the resulting absorbent product 20 wherein the fastening components 82 are bonded to the inner surface 28. The embodiments in FIGS. 23 and 25 show the resulting absorbent product 20 wherein the fastening components 82 are bonded to the outer surface 30. FIG. 26 is a side perspective view of a partially fastened absorbent product 20 having the refastenable hook and loop fasteners with dual lap side seams 100 and standing butt seams 88, as illustrated in FIG. 25.

The absorbent chassis 32 and the fastening system 80 together define a refastenable product having a waist opening 50 and a pair of leg openings 52. When the fastening system is engaged, the refastenable product includes a pair of elastomeric front side panels 34 extending from the waist opening 50 to each leg opening 52, a pair of elastomeric back side panels 134 extending from the waist opening 50 to each leg opening 52, a pair of standing butt seams 88, and/or lap side seams 100 (FIGS. 1, 15, 20, 26) extending from the waist opening 50 to each leg opening 52 and positioned between the elastomeric front and back side panels 34, 134, an elastomeric front waistband 54 disposed on the front side 22 and positioned between the pair of elastomeric front side panels 34, an elastomeric back waistband 56 disposed on the back side 24 and positioned between the pair of elastomeric back side panels 134, and at least a pair of the leg elastic members 58 which partially encircle each leg opening 52. More preferably, more than one leg elastic member 58 partially or fully encircles each leg opening 52. Each leg elastic member 58 extends from adjacent an elastomeric front side panel 34 on the front side 22 to adjacent an elastomeric back side panel 134 on the back side 24.

As described herein, the various components of the absorbent garment 20 can be integrally assembled together employing various types of suitable attachment means, such as adhesive, sonic and thermal bonds or combinations thereof. The resulting product is an absorbent garment having refastenable side seams that can be opened for donning or removal at either side of the garment.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent garment, comprising:
 a chassis comprising a front panel including a pair of front side regions and a back panel including a pair of back side regions wherein each of the front and back side regions has an average length dimension that is at least 20 percent of an overall length dimension of the chassis, and defining a waist opening and first and second leg openings;
 a first dual refastenable seam extending from the waist opening to the first leg opening between the front panel and the back panel; and
 a second dual refastenable seam extending from the waist opening to the second leg opening between the front panel and the back panel;
 wherein each of the first and second dual refastenable seams comprises a first fastening component bonded to the front panel and a second fastening component bonded to the back panel, and a mating fastening component releasably attached to the first and second fasting components on the front panel and the back panel, the mating fastening component comprising two separate pieces of material bonded together to form a standing butt seam.

2. The absorbent garment of claim 1 wherein each of the first fastening components is bonded to an inner surface of the front panel and each of the second fastening components is bonded to an inner surface of the back panel.

3. The absorbent garment of claim 1 wherein each of the first fastening components is bonded to an outer surface of the front panel and each of the second fastening components is bonded to an outer surface of the back panel.

4. The absorbent garment of claim 1 wherein the fastening components comprise a hook material and the mating fastening components comprise a loop material.

5. The absorbent garment of claim 1 wherein the fastening components comprise a loop material and the mating fastening components comprise a hook material.

6. The absorbent garment of claim 1 wherein the chassis comprises an elastic material.

7. The absorbent garment of claim 1, comprising a diaper.

8. The absorbent garment of claim 1, comprising swim wear.

9. The absorbent garment of claim 1, comprising child training pants.

10. The absorbent garment of claim 1, comprising an adult incontinence garment.

11. The absorbent garment of claim 1, wherein the front panel comprises a pair of stretchable front side regions including the fastening components.

12. The absorbent garment of claim 1, wherein the back panel comprises a pair of stretchable back side regions including the mating fastening components.

13. The absorbent garment of claim 6 wherein each of the first fastening components comprises a first longitudinal edge area and a second longitudinal edge area opposite the first longitudinal edge area, and the first longitudinal edge area is bonded to a distal edge of the front panel, and the second longitudinal edge area is not bonded to the front panel such that the second longitudinal edge area extends away from the front panel.

14. The absorbent garment of claim 1 wherein each of the second fastening components comprises a first longitudinal edge area and a second longitudinal edge area opposite the first longitudinal edge area, and the first longitudinal edge area is bonded to a distal edge of the back panel, and the second longitudinal edge area is not bonded to the back panel such that the second longitudinal edge area extends away from the back panel.

* * * * *

UNITED STATES PATENT AND TRADEMARK OFFICE
CERTIFICATE OF CORRECTION

PATENT NO.   : 6,817,994 B2
DATED        : November 16, 2004
INVENTOR(S)  : Robert Lee Popp It is certified that error appears in the above-identified patent and that said Letters Patent is hereby corrected as shown below:

<u>Column 20,</u>
Line 1, please change "The absorbent garment of claim 6" to -- The absorbent garment of claim 1 --.

Signed and Sealed this

Fifteenth Day of March, 2005

JON W. DUDAS
*Director of the United States Patent and Trademark Office*